United States Patent
Thompson et al.

(10) Patent No.: US 9,625,431 B2
(45) Date of Patent: *Apr. 18, 2017

(54) LIQUID GAS VAPORIZATION AND MEASUREMENT SYSTEM AND METHOD

(71) Applicant: Mustang Sampling, LLC, Ravenswood, WV (US)

(72) Inventors: Kenneth O. Thompson, Ravenswood, WV (US); Walter F. Gerhold, Dallas, NC (US)

(73) Assignee: Mustang Sampling, LLC, Ravenswood, WV (US)

( * ) Notice: Subject to any disclaimer, the term of this patent is extended or adjusted under 35 U.S.C. 154(b) by 338 days.

This patent is subject to a terminal disclaimer.

(21) Appl. No.: 14/261,607

(22) Filed: Apr. 25, 2014

(65) Prior Publication Data

US 2014/0230521 A1    Aug. 21, 2014

Related U.S. Application Data

(63) Continuation of application No. 12/971,035, filed on Dec. 17, 2010, now Pat. No. 8,713,995, which is a (Continued)

(51) Int. Cl.
*G01N 30/32* (2006.01)
*G01N 33/00* (2006.01)
(Continued)

(52) U.S. Cl.
CPC .......... *G01N 33/0016* (2013.01); *F17C 6/00* (2013.01); *F17C 9/00* (2013.01); *F17C 13/02* (2013.01);
(Continued)

(58) Field of Classification Search
USPC .............................................. 73/61.55–61.57
See application file for complete search history.

(56) References Cited

U.S. PATENT DOCUMENTS 2,665,239 A    1/1954    Howard et al.
3,609,983 A    10/1971    Lofredo et al.
(Continued)

FOREIGN PATENT DOCUMENTS

EP            0134690 A2    3/1985

OTHER PUBLICATIONS

European App. No. EP 05769462.2, Supplementary European Search Report, dated Apr. 5, 2012.
(Continued)

*Primary Examiner* — Michael A Lyons
*Assistant Examiner* — Alexander Mercado
(74) *Attorney, Agent, or Firm* — Cahn & Samuels, LLP

(57) ABSTRACT

A liquid gas vaporization and measurement system, and associated method, for efficiently vaporizing a continuous sample of liquid gas, such as liquid natural gas (LNG), and accurately determining the constituent components of the gas. A constant flow of liquid gas sampled from a mass storage device is maintained in a vaporizing device. Within the vaporizing device the liquid gas is flash vaporized within heated narrow tubing. The liquid gas is converted to vapor very quickly as it enters one or more independently operating vaporizer stages within the vaporizing device. The vapor gas is provided to a measuring instrument such as a chromatograph and the individual constituent components and the BTU value of the gas are determined to an accuracy of within +/−0.5 mole percent and 1 BTU, respectively.

7 Claims, 4 Drawing Sheets

Related U.S. Application Data continuation of application No. 12/362,846, filed on Jan. 30, 2009, now Pat. No. 7,882,729, which is a continuation of application No. 11/358,724, filed on Feb. 22, 2006, now Pat. No. 7,484,404.

(60) Provisional application No. 60/654,472, filed on Feb. 22, 2005.

(51) Int. Cl.
*F17C 6/00* (2006.01)
*F17C 9/00* (2006.01)
*F17C 13/02* (2006.01)
*G01N 1/10* (2006.01)
*G01N 1/22* (2006.01)
*G01N 33/22* (2006.01)

(52) U.S. Cl.
CPC .............. *G01N 1/10* (2013.01); *G01N 1/22* (2013.01); *G01N 33/225* (2013.01); *F17C 2221/033* (2013.01); *F17C 2223/0161* (2013.01); *F17C 2223/033* (2013.01); *F17C 2223/046* (2013.01); *F17C 2225/0123* (2013.01); *F17C 2225/0161* (2013.01); *F17C 2225/033* (2013.01); *F17C 2225/035* (2013.01); *F17C 2227/0135* (2013.01); *F17C 2227/0302* (2013.01); *F17C 2227/0311* (2013.01); *F17C 2227/0318* (2013.01); *F17C 2227/0332* (2013.01); *F17C 2227/0393* (2013.01); *F17C 2250/0456* (2013.01); *F17C 2270/0105* (2013.01); *F17C 2270/0136* (2013.01); *G01N 33/22* (2013.01); *G01N 2001/105* (2013.01); *G01N 2001/2261* (2013.01)

(56) References Cited

U.S. PATENT DOCUMENTS

| | | |
|---|---|---|
| 3,661,202 A | 5/1972 | Moore, Jr. |
| 3,933,030 A | 1/1976 | Forster et al. |
| 3,976,450 A | 8/1976 | Marcote et al. |
| 4,296,637 A | 10/1981 | Calamur et al. |
| 4,519,213 A | 5/1985 | Brigham et al. |
| 4,974,453 A | 12/1990 | Hohorst |
| 5,321,984 A | 6/1994 | Stroupe |
| 5,343,747 A | 9/1994 | Rosen |
| 5,363,874 A | 11/1994 | Henszey et al. |
| 5,505,782 A | 4/1996 | Stauffer |
| 5,544,276 A | 8/1996 | Loux et al. |
| 5,596,154 A | 1/1997 | Baughman |
| 5,918,595 A | 7/1999 | Olsson et al. |
| 6,042,634 A | 3/2000 | Van Tassel et al. |
| 6,299,767 B1 | 10/2001 | Dourdeville |
| 6,408,895 B1 | 6/2002 | Beam |
| 6,598,408 B1 | 7/2003 | Nierenberg |
| 6,827,046 B2 | 12/2004 | Welle |
| 6,848,502 B2 | 2/2005 | Bishop et al. |
| 6,981,850 B1 | 1/2006 | Maltbie et al. |
| 7,337,616 B2 | 3/2008 | Meneses et al. |
| 8,347,694 B2 | 1/2013 | Welker et al. |
| 2003/0228707 A1 | 12/2003 | Meneses et al. |

OTHER PUBLICATIONS

European App. No. EP 06735575, Supplementary European Search Report, dated Aug. 7, 2015.
European Application No. 06735575.0, Opinion.
United States International PCT App. No. PCT/US 06/05981, ISR/WO dated Sep. 24, 2007.
Coyle, David, et al.,: "Processes and Pump Services in the LNG Industry," Proceedings of the Twenty-Second International Pump Users Symposium, 2005, pp. 179-185.
Foss, Michelle M. Ph. D.,: "Introduction to LNG; An Overview on liquefied natural gas (LNG), its properties, the LNG industry, safety considerations," Energy Economics Research at the Bureau of Economic Geology, Center for the Energy Economics, Jan. 2003.
Tarlowski, Janusz, et al.,: "LNG Import Terminals—Recent Developments," 2005.
United State of America Federal Energy Regulatory Commission, "Notice of Availability of Staff's Responses to Comments on the Consequence Assessment Methods for Incidents Involving Releases from Liquefied Natural Gas Carriers," Jun. 18, 2004.
Energy Information Administration, "U.S. Natural Gas Markets: Mid Term Prospects for Natural Gas Supply," Dec. 2001.
Energy Information Administration, Office of Oil and Gas, "U.S. LNG Markets and Uses," Jan. 2003.
Stockwell, Peter B., et al.,: "Mercury Measurements in the Fossil Fuels, Particularly Petrochemicals," Journal of ASTM International, Jan. 2006, vol. 3, No. 1.

LIQUID GAS VAPORIZATION AND MEASUREMENT SYSTEM AND METHOD

I. CROSS REFERENCE TO RELATED APPLICATIONS

This This application is a continuation application of U.S. Ser. No. 12/971,035 filed Dec. 17, 2010, U.S. Pat. No. 8,713,995, which is a continuation application of U.S. Ser. No. 12/362,846 filed on Jan. 30, 2009, now U.S. Pat. No. 7,882,729, which is a continuation application of U.S. Ser. No. 11/358,724 filed on Feb. 22, 2006, now U.S. Pat. No. 7,484,404, and claims priority of Provisional Application Ser. No. 60/654,472, filed on Feb. 22, 2005, the entire contents of the patents and the provisional application are incorporated herein by reference.

II. FIELD OF THE INVENTION

This invention relates generally to a system and method for the efficient vaporization and measurement of liquid natural gas (LNG). More particularly, the invention relates to a system and method for continuously and efficiently vaporizing an LNG shipment, or portion thereof, into its gaseous form in order to accurately determine the constituent components and British Thermal Unit (BTU) value of the LNG shipment.

III. BACKGROUND OF THE INVENTION

Natural gas is a combustible, gaseous mixture of several different hydrocarbon compounds and is typically extracted from deep underground reservoirs formed by porous rock. The composition of natural gas extracted from different reservoirs varies depending on the geographic location of the reservoir. In fact, it is not entirely uncommon for the composition of gas extracted from a single given reservoir to vary to an extent. Regardless of any variations, however, the primary component of natural gas is methane, a colorless, odorless, gaseous saturated hydrocarbon. Methane usually accounts for 80% to 95% of any natural gas sample and the balance is composed of varying amounts of ethane, propane, butane, pentane and other hydrocarbon compounds.

Natural gas is used extensively in residential, commercial and industrial applications. It is the dominant energy used for home heating with well over half of American homes using natural gas. The use of natural gas is also rapidly increasing in electric power generation and cooling, and as a transportation fuel.

Natural gas, like other forms of heat energy, is measured in British thermal units or Btu. One Btu is equivalent to the heat needed to raise the temperature of one pound of water by one degree Fahrenheit at atmospheric pressure.

A cubic foot of natural gas has about 1,027 BTU. Natural gas is normally sold from the wellhead, i.e., the point at which the gas is extracted from the earth, to purchasers in standard volume measurements of thousands of cubic feet (Mcf). However, consumer bills are usually measured in heat content or therms. One therm is a unit of heating equal to 100,000 BTU.

Three separate and often independent segments of the natural gas industry are involved in delivering natural gas from the wellhead to the consumer. Production companies explore, drill and extract natural gas from the ground; transmission companies operate the pipelines that connect the gas fields to major consuming areas; and distribution companies are the local utilities that deliver natural gas to the customer.

In the United States alone, natural gas is delivered to close to 200 million consumers through a network of underground pipes that extends over a million miles. To produce and deliver this natural gas there are over a quarter-million producing natural gas wells, over one hundred natural gas pipeline companies and more than a thousand local distribution companies (LDCs) that provide gas service to all 50 states.

Prior to regulatory reform, which essentially restructured the industry, producers sold gas to the pipeline companies, who sold it to the LDCs, who sold it to residential and other customers. Post-regulation, however, pipeline companies no longer purchase gas for resale. Instead, the pipeline companies merely transport gas from sellers, such as producers or marketers, to buyers, such as electric utilities, factories and LDCs. Thus, the LDCs now can choose among a variety of sellers of natural gas, whereas before they could only buy gas from one source, i.e., the pipeline company. Further, some states have implemented additional restructuring which renders the LDCs subject to regulation by State public utility commissions. Prior to these additional state regulations, an LDC's residential customers could only buy gas from one source, i.e., the LDC. After state regulation, however, residential customers can choose a different supplier other than their LDC from which to buy the gas. The consumer's LDC, as the owner/operator of the distribution network, delivers the gas to the consumer, as before, but the LDC only charges the consumer for delivery of the gas and the independent supplier bills for the gas.

Thus, natural gas is very important to the U.S. energy supply. Consumption of natural gas in the United States, however, has increased beyond the available supply of domestic natural gas. One available option to increase supply is to increase imports of liquefied natural gas (LNG).

More particularly, according to one estimate natural gas consumption in the United States is expected to increase from about 22 trillion cubic feet (Tcf) in 2004 to almost 31 Tcf by 2025. Accordingly, domestic production combined with imports via pipeline from Canada will be insufficient to meet the demand. In response, a small but growing percentage of gas supplies are imported and received as LNG via tanker ships.

LNG is produced by taking natural gas from a production field, removing impurities, and liquefying the natural gas. In the liquefaction process, the gas is cooled to a temperature of approximately −260 degrees F. One volume of this condensed liquid form of natural gas occupies about $\frac{1}{600}$th of the volume of natural gas at a stove burner tip. The LNG is loaded onto double-hulled ships which are used for both safety and insulating purposes. Once the ship arrives at the receiving port, the LNG is typically off-loaded into well-insulated storage tanks. Vaporization or regasification is used to convert the LNG back into its gas form, which enters the domestic pipeline distribution system and is ultimately delivered to the end-user.

Because LNG is sold in accordance with its BTU value, accurate analysis of the BTU value of any particular LNG shipment, as well as analysis of the constituent components of the LNG, as it is off-loaded from a respective tanker ship is crucial. For example, to determine an expected price for a particular shipment, when LNG is loaded onto a tanker ship at an overseas location, such as Trinidad and Tobago where large natural gas reserves are found, the supplier calculates the Btu value of the LNG as it is loaded into the hull of the ship. Additionally, because the Btu value of the shipment will likely change in transit, for example due to vaporization of some of the LNG while it is sitting in the hull of the ship, the recipient of the LNG shipment also desires to accurately determine the Btu value of the delivered LNG shipment. The operator of the tanker ship carrying the LNG shipment is also keenly interested in accurate BTU measurement of both the loaded LNG as well as the off-loaded LNG as the shipper typically burns the LNG vaporized in transit to run the ship and, thus, is responsible for cost of the LNG vaporized in transit.

Accordingly, it is desired to provide a method and system for accurately measuring the BTU value of an LNG shipment as it is off-loaded from a tanker ship.

One related art method that addresses the issue discussed above is disclosed in U.S. Pat. No. 3,933,030 to Forster et al. In Forster, a system is disclosed for the continuous monitoring of the density of cryogenic liquids, such as LNG. In accordance with the Forster system the dielectric constant of stored LNG is instantaneously determined by the use of sensors in the storage tank. Multiple sensors, each comprising a capacitor probe, are placed at various locations within the storage tank. The sensors are then operable to instantaneously measure the dielectric constant of the liquid within the tank and from this data the density of the liquid in the tank is determined. From the density measurement it is possible to then calculate the BTU per unit volume and appropriate charges per BTU can be calculated.

Several problems arise from a system such as the one disclosed in Forster, however. For example, the accuracy of the BTU measurement is unacceptable for today's standards.

Other, more recent, related art systems utilize chromatograph technology to determine the BTU value of LNG. These related art systems, however, also suffer from poor accuracy and/or high levels of maintenance. For example, one known system utilizes a method in which liquid gas is circulated in tubes that are submersed in a heated solution. The heat in the solution, in turn, heats the tubing which vaporizes the liquid gas. This method of vaporization is very inefficient, however, and the accuracy of any resulting BTU measurements are unacceptable, e.g., less than 5 BTU, that is, the swing on the BTU measurement is greater than 5 BTU.

Accordingly, it is desired to provide a system that does not suffer from at least these problems and which can provide a much more accurate and detailed assessment of liquefied gas and at the same time requires less maintenance than current systems.

IV. SUMMARY OF THE INVENTION

Illustrative, non-limiting embodiments of the present invention may overcome the aforementioned and other disadvantages associated with related art liquid gas vaporization and measurement systems. Also, the present invention is not necessarily required to overcome the disadvantages described above and an illustrative non-limiting embodiment of the present invention may not overcome any of the problems described above.

It is an object of the present invention to provide a novel system and method for efficiently and accurately sampling and measuring liquid gas.

To achieve the above and other objects an embodiment in accordance with the invention includes a system for vaporizing and measuring liquid gas, the system comprising a transmission device operable to transmit liquid gas, a measurement device operable to continuously extract at least a portion of the liquid gas from the transmission device while it is being transmitted by the transmission device, convert the extracted liquid gas from liquid form to vapor form and determine the constituent components of the vapor gas.

Another embodiment of the invention includes a device for sampling and vaporizing liquid gas, the device comprising a first stage vaporizer operable to receive liquid gas at a first flow rate from an input port and convert the received liquid gas into vapor gas, a second stage vaporizer operable to receive liquid gas at a second flow rate and convert the received liquid gas into vapor gas, an accumulator connected to the first and second stage vaporizers and operable to receive and store the vapor gas, and a third stage vaporizer connected to the accumulator and operable to receive stored vapor gas from the accumulator and control the pressure of the received vapor gas to be within a desired pressure range. In this exemplary embodiment stainless steel tubing is used to convey the gas throughout the system. Additionally, the tubing within the second stage vaporizer has a diameter as small as one-eight inch and is spirally wound around one or more cartridge heaters to efficiently flash vaporize the liquid gas. A constant flow of gas through the system is also maintained by using a speed loop.

An even further embodiment of the invention includes A method of measuring the constituent components of liquid gas, the method comprising receiving the liquid gas into a vaporizing device, selectively directing the received liquid gas into one or more of a first and second stage vaporizer within the vaporizing device, converting the liquid gas directed to one or more of the first and second stage vaporizers into vapor gas and accumulating the vapor gas in a relatively small storage device, for example, one-half cubic foot volume. The exemplary method further includes outputting the vapor gas accumulated in the storage device and directing the outputted vapor gas from the storage device to a measuring device operable to determine the constituent components of the vapor gas.

As used herein "gas" means any type of gaseous matter capable of pipe transmission, including natural gas, organic gases, industrial gases, medical gases, monomolecular gases, gas mixtures, and equivalents.

As used herein "connected" includes physical, whether direct or indirect, permanently affixed or adjustably mounted. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of specific exemplary embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a novel liquid gas vaporization and measurement system and a method thereof for providing significantly augmented efficiencies while mitigating problems of the prior art.

V. BRIEF DESCRIPTION OF THE DRAWINGS

The aspects of the present invention will become more readily apparent by describing in detail illustrative, non-limiting embodiments thereof with reference to the accompanying drawings, in which.

VI. DETAILED DESCRIPTION OF ILLUSTRATIVE, NON-LIMITING EMBODIMENTS

Exemplary, non-limiting, embodiments of the present invention are discussed in detail below. While specific configurations and dimensions are discussed to provide a clear understanding, it should be understood that the disclosed dimensions and configurations are provided for illustration purposes only. A person skilled in the relevant art will recognize that, unless otherwise specified, other dimensions and configurations may be used without departing from the spirit and scope of the invention.

Figure 1:
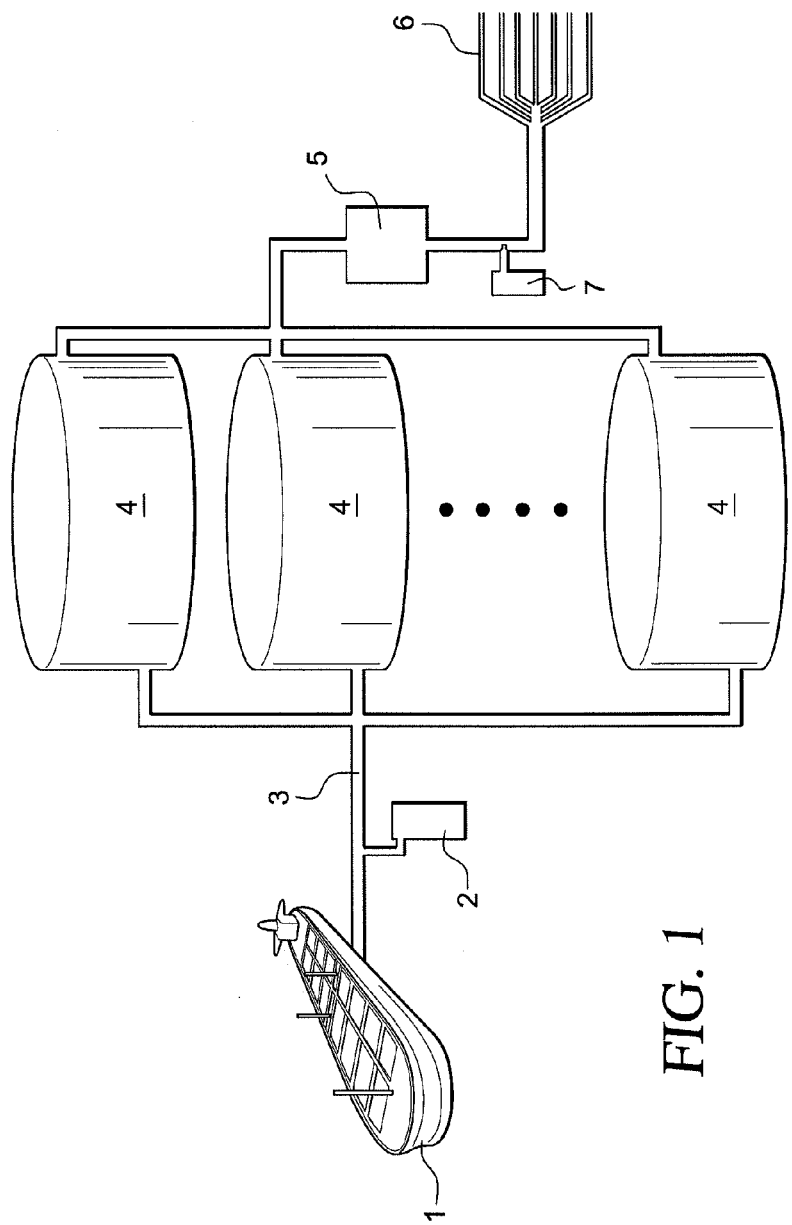
FIG. 1 is block diagram illustrating a system in accordance with the present invention.

FIG. 1 is an exemplary block diagram illustrating a system in accordance with the present invention. As shown, the system of FIG. 1 comprises a tanker ship 1 carrying a shipment of liquefied natural gas (LNG). In accordance with this embodiment, tanker 1 docks into a port where the shipment of LNG is to be off-loaded to storage tanks before being regassified and shipped to various gas customers. According to the present embodiment tanker ship 1 is a marine vessel. However, a skilled artisan would understand that tanker ship 1 could also be any vehicle or device capable of transporting or storing liquefied gas, such as a tanker truck or other storage device. To accurately measure the BTU value of the LNG being offloaded from tanker 1, a vaporizer unit 2 in accordance with the present invention and discussed in detail below, is connected in-line with the LNG being transferred from tanker 1 to storage tank 4 via, for example, pipeline 3. As LNG is transported in pipeline 3 to storage tank 4, at least a portion of the LNG is delivered to vaporizer unit 2 to be analyzed and measured.

As discussed in detail below, vaporizer unit 2 continuously receives an amount of LNG from pipeline 3, vaporizes the LNG into gaseous form and analyzes the vaporized LNG to very accurately determine the constituent components of the gas, for example, via a chromatograph. Thus, on a continuous basis, that is, continually as the LNG is being transported in pipe 3 to storage tank 4, the real-time, or at least very near-real-time, BTU value for the LNG being transported is calculated. Accordingly, an accurate accounting of the LNG and its BTU value and/or cost is determined for the LNG being offloaded or otherwise transferred into storage tank 4. It should be noted that not only is the placement of the vaporizer unit 2 important for such calculations, e.g., the LNG vaporizer unit 2 should be as close to the LNG discharge line as possible, but also the structure and configuration of the vaporizer unit additionally contributes to extremely accurate calculations of the BTU value of the LNG.

The LNG from which the representative sample is extracted and used in unit 2 is pumped or otherwise transferred into storage tank 4 where it is kept at the appropriate pressure and temperature to reduce both the risk of explosion as well the risk of inadvertent vaporization into the atmosphere. The LNG resides in tank 4 until it is needed, e.g., in the form of natural gas vapor for consumers, upon which time the LNG is pumped from tank 4 and regassified, or vaporized, by degasification device 5. Degasification or vaporization device 5 can be any one or combination of known vaporization devices. For example, vaporization device 5 can be an open rack vaporizer (ORV), a submerged combustion vaporizer (SCV), a combined heat and power unit with SCV (CHP-SCV), an ambient air-heated vaporizer or any combination of these or other types of vaporizers.

After the bulk-stored LNG for consumption by consumers has been converted into vapor gas, the vapor gas is transferred, for example, via a pipeline system 6, to local distributors, i.e., the LCDs, and to the end-users. At any point after the LNG has been turned back into gas by vaporization device 5, the gas can be, but in accordance with the invention does not have to be, sampled and conditioned via a Gas Sample Conditioning System 7 such as the one disclosed in U.S. patent application Ser. No. 11/169,619, which assigned to the same assignee as the present invention.

Figure 2:
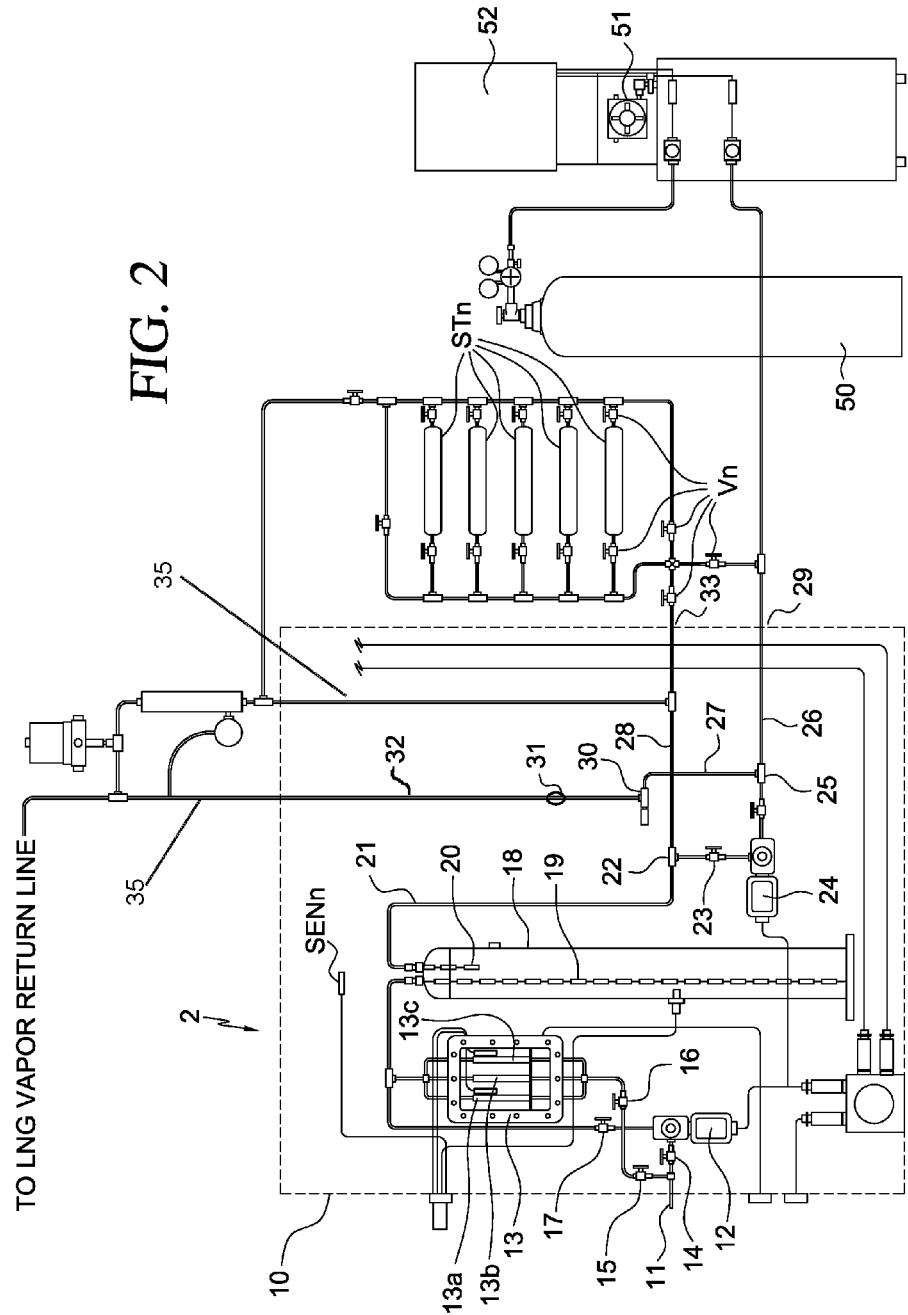
FIG. 2 is a schematic diagram of a vaporizing and measurement device in accordance with the present invention.

FIG. 2 is a schematic diagram of an LNG vaporizer unit 2 in accordance with the present invention. In accordance with the exemplary embodiment of vaporizer unit 2 shown in FIG. 2, LNG is input to cabinet 10 via LNG inlet port 11 which comprises, for example, stainless steel tubing having a diameter of ¼-inch. Cabinet 10 comprises an enclosure for providing protection from the elements, such as rain, snow, ice, wind, etc. to the individual components within. Inlet port 11 is connected to ¼ inch tubing within enclosure 10 which, in turn connects to first and second vaporizer stages 12, 13, respectively. The first and second vaporizer stages 12 and 13 operate independently to vaporize LNG into its gaseous form. In particular, LNG enters inlet port 11 in liquid form at a temperature of approximately −249° F., although a person of ordinary skill in the art would understand that LNG remains in liquid form at temperatures generally below 100° F. and, thus, consistent with the invention other temperatures are possible as well. The LNG input to inlet port 11 is then selectively channeled to one or both of the first and second stage vaporizing devices 12, 13.

Because LNG begins to vaporize as soon as it begins to heat up and the longer a tube carrying LNG is, the warmer the LNG gets, the tubes carrying the LNG within enclosure 10 and connecting the various devices within the vaporizer unit 2 are kept as short as possible, i.e., to minimize the amount of vaporization that takes place prior to the LNG entering one or both of the first and second stage vaporizing devices 12, 13. Also, insulation, such as two inches of polyisocurnat insulating material, is placed on and around the ¼ inch tubing that carries the LNG from the input port to each of the first and second stage vaporizer devices.

Valve 14 is attached to ¼ inch tubing that connects the inlet port 11 to first stage vaporizer 12. Valve 14 operates to shut-off or open the path for LNG to flow into the first stage 12. The first stage vaporizer 12 uses a heated spiraled entry (not shown) as well as exiting heat transfer and the gas output exits at approximately 100° F. at a flow rate of 18 SCFH (standard cubic feet per hour).

As gas exits the first stage vaporizer 12 it travels through ¼ inch tubing to the top of the accumulator 18. The accumulator 18 is a gas cylinder capable of storing natural gas vapor.

The second stage vaporizer 13 is connected to the inlet port 11 via additional ¼ inch tubing and one or more valves 15, 16. The second stage vaporizer 13 comprises a plurality cartridge heaters 13a, 13b, 13c around each of which is wound a length of ⅛ inch tubing. For example, as shown in FIG. 2, three cartridge heaters each have respective lengths of ⅛ inch tubing wound around their outer surface. The tubing around each of the heaters is connected to the ¼ inch tubing carrying the LNG to the stage 2 vaporizer.

It should be noted that valves 14-17, ideally, are suitable for cryogenic operation due to the low temperatures of the LNG flowing therethrough. Accordingly, valves 14-17 are optional and not necessarily required for the operation of the LNG cabinet.

Figure 3:
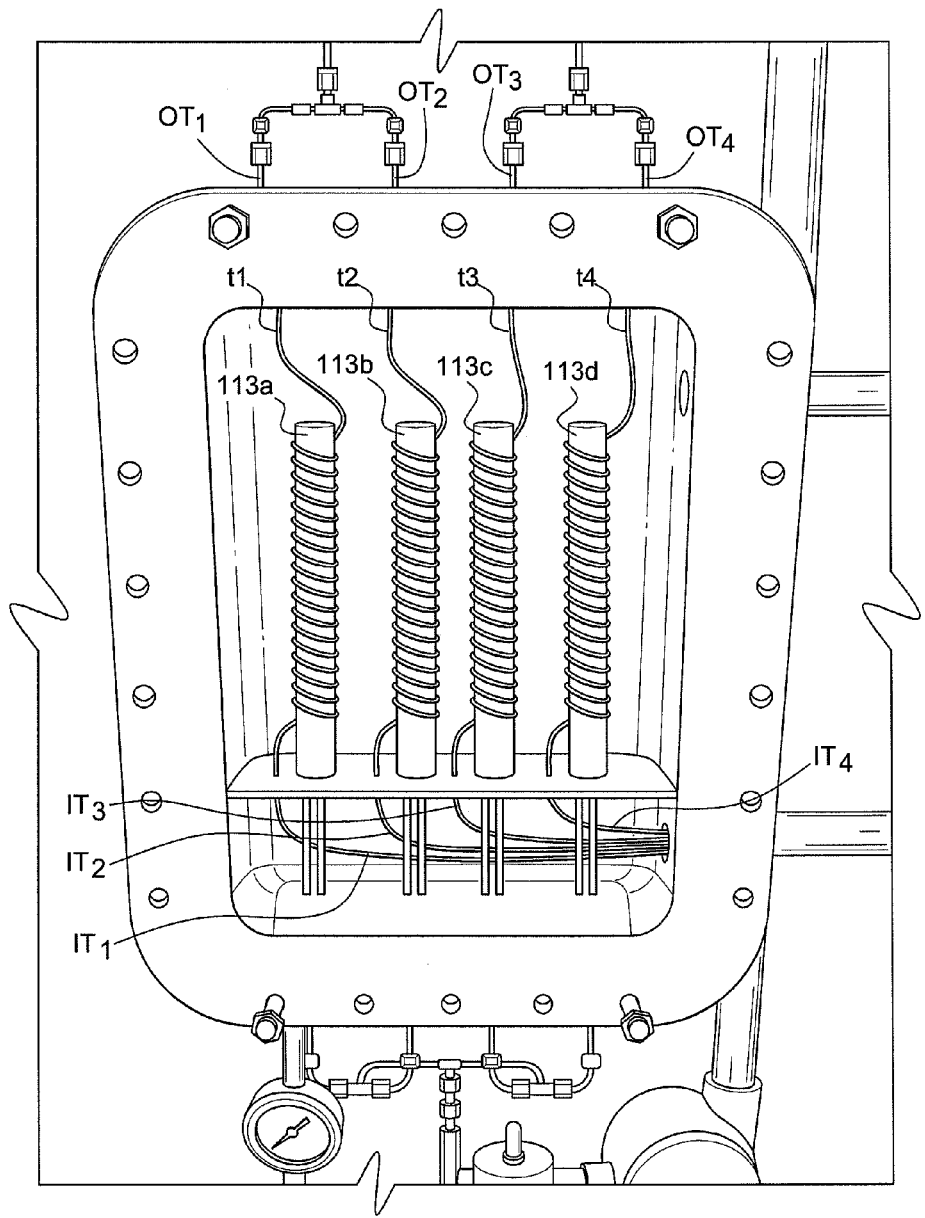
FIG. 3 is a drawing of an embodiment of a second stage vaporizer according to the invention.

FIG. 3 is a close-up view of an exemplary second stage vaporizer similar to second stage vaporizer 13 shown in FIG. 2. The second stage vaporizer shown in FIG. 3 utilizes four cartridge heaters 113a through 113d, as opposed to the three cartridge heaters shown in regard to the embodiment of FIG. 2. Otherwise, the second stage vaporizer shown in FIG. 3 is identical to the one depicted in FIG. 2. Also, as shown in FIG. 3, a respective length of ⅛ inch tubing t1-t4 is wound around each cartridge heater 113a-113d.

Referring to FIG. 3, the LNG enters the second stage vaporizer at the bottom via four respective ¼ inch input tubes $IT_1$-$IT_4$. Within the second stage vaporizer the LNG is then directed into four respective ⅛ inch tubes, t1-t4. Each tube t1-t4 is wound spirally around a respective cartridge heater 113a-113d that quickly heats the LNG within the narrow spiral tubing converting the LNG within the tubes to vapor gas. The vapor gas from each of the respective ⅛ inch tubes is then directed into a respective output tube $OT_1$-$OT_4$ and the vapor gas is directed into the accumulator in similar fashion as discussed with respect to FIG. 2.

Referring back to FIG. 2, respective valves (not shown) control the flow of LNG into the respective tubing wound around each of the cartridges 13a, 13b and 13c. In particular, the flow into each of the ⅛ inch tubes is controlled such that the total flow of LNG in the ¼ inch tube flows through the three ⅛ inch tubes in any combination, e.g., ⅓ in each of the three ⅛ inch tubes, ½ in each of two ⅛ inch tubes and none in the third ⅛ inch tube, etc. Further, it should be noted that valves 14-17 are also configured such that the LNG that enters the input port 11 can be directed in any desired percentage to both the first and second stage vaporizers 12 and 13. For example, it is possible to direct any amount, X, (where X=0% to 100%) of the LNG entering port 11 into the first or second stage vaporizer and an amount Y (where Y=100−X) into the other of the first and second stage vaporizers. Accordingly, it is possible to run the vaporizer cabinet 10 even if one of the first or second stage vaporizers should fail.

It should also be noted that even though the present embodiment includes three cartridge heaters, e.g., 13a, 13b and 13c, the invention is not limited to this configuration. One of ordinary skill would know that provided sufficient LNG/vapor flow through the second stage vaporizer, any number of cartridge heaters can be used.

As vapor gas exits the second stage vaporizer 13 the vapor gas is carried by ¼ inch tubing to the accumulator 18. As shown, the vapor gas enters the accumulator 18 at the top and is carried via a tube 19 inside the accumulator to an interior location within the accumulator 18. As vapor gas exits the tube 19 it is directed toward the inside wall of the accumulator 18. As the vapor gas impinges the interior wall of the accumulator 18 it is mixed thoroughly with any gas already existing within the tank. Tube 19 is of variable length and can expel vapor gas within the accumulator 18 at any height within the accumulator 18. However, in accordance with the present embodiment, the output of tube 19 is approximately 80 to 90 percent down toward the bottom of the accumulator 18.

Thoroughly mixed vapor gas within the accumulator 18 is removed via additional tubing 20 near the top of the accumulator 18. The removed gas is carried in ¼ inch tubing 21 to a "T" joint 22. At "T" 22 the vapor gas is either directed into tubing 28, through valve 23 or some combination of both. Valve 23 controls the amount of vapor gas permitted to flow into vaporizer stage 3 (ref. no. 24). Vaporizer stage 3 essentially operates as a pressure reducer. That is, stage 3 (24) controls the pressure for vapor permitted to enter tube 26, which carries the sample vapor gas to a chromatograph, discussed later. For example, in accordance with one scenario, vaporizer cabinet 10 is positioned in close proximity to a pipeline header carrying LNG from a tanker ship to on or more storage tanks (See, e.g., FIG. 1). As the storage tank 4 begins to fill with LNG the pressure within pipe 3 must increase in order to continue to fill tank 4. As the pressure in pipe 3 increases, so does the pressure in the sample line to cabinet 10 and through the various stages of vaporization. Accordingly, stage 3 (24) operates to control the pressure of vapor gas into tube 26. For instance, the pressure in tube 21 and through valve 23 might be somewhere around 10-65 PSI. Pressures in this range are typically detrimental to chromatograph devices and, thus, stage 3 reduces the pressure to an acceptable level, such as 5-10 PSIG. Vapor gas at an acceptable pressure is then output from cabinet 10 at port 29.

According to the embodiment shown in FIG. 2, a tube 27 is connected to a "T" joint 25 which is further connected to tube 26. Tube 27 is further connected to a relief valve 30 which releases vapor gas therethrough in the event the pressure in tube 26 should exceed a predetermined maximum value. That is, relief valve 30 normally does not permit gas to flow through it when the pressure in tube 26 is below a certain value. If, however, the pressure in tube 26 exceeds this value, relief valve 30 opens and releases an amount of gas necessary to reduce the pressure in tube 26 to below the predetermined value. Any vapor gas released by relief valve 30 goes through one-way valve 31 and is provided to an LNG vapor return line via tube 32.

Any vapor gas outputted from accumulator 18 that does not pass through valve 23 and into stage 3 (24) enters tube 28 and exits cabinet 10 at port 33. One or more valves, V1-V14, are provided to control gas flowing into sample tanks ST1-ST5. For example, one or more sample tanks (e.g., ST1-ST5) are provided to store samples of vapor gas withdrawn from accumulator 18. For instance, different samples can be taken and stored at different times, such as at various times during the overall unloading process of a load of LNG from a tanker ship as it is transferred into a storage tank. Valves Vn are individually opened or closed in order to store samples in sample tanks STn at appropriate times.

The gas stored in any one of the sample tanks STn can be controlled to come directly from the output of accumulator 18 or it can be a sample taken from the output of vaporizer stage 3 (24). For example, during periods when a tanker ship is not being off-loaded, the LNG being inputted to input port 11 is recirculated LNG from a storage tank, such as tank 4 shown in FIG. 1. By recirculating LNG from storage tank 4 in this manner, a constant pressure (and temperature) is maintained in the lines of vaporizer 10. Because the pressure in the main line 3 is not significantly altered, as compared to the situation when a tanker is being off-loaded as described above, it is not necessary to regulate, or reduce, the pressure using stage 3 (24).

Thus, under these circumstances sample LNG is vaporized by one or more of stages 1 and 2 (12 and 13 in FIG. 2), vapor is collected and mixed in accumulator 18 and the vapor is drawn off through tubes 21 and 28 and out cabinet 10 through port 33. The vapor from the recirculated LNG sample is then directed to either sample tanks STn, bypassed around sample tanks STn and returned to the LNG vapor return line 35 or channeled through one of the valves Vn and into chromatograph 52 via optional liquid block 51. For example, optional liquid block 51 is used for natural gas production gas where liquids are typically present. Similarly, if desired, by opening or closing the appropriate combination of valves Vn, the vapor gas outputted from stage 3 (24) is directed to the sample tanks STn, bypassed around sample tanks STn and returned to the LNG vapor return line 35 or channeled through one of the valves Vn and into chromatograph 52 via optional liquid block 51.

In order to calibrate chromatograph 52, a tank of calibration gas with a known composition is stored in cal tank 50. Accordingly, when it is desired to calibrate the chromatograph 52, the vapor gas outputted from cabinet 10, through either port 29 or port 33, is shut-off automatically and calibration gas from tank 50 is applied to the chromatograph 52.

While various aspects of the present invention have been particularly shown and described with reference to the exemplary, non-limiting, embodiments above, it will be understood by those skilled in the art that various additional aspects and embodiments may be contemplated without departing from the spirit and scope of the present invention.

Figure 4:
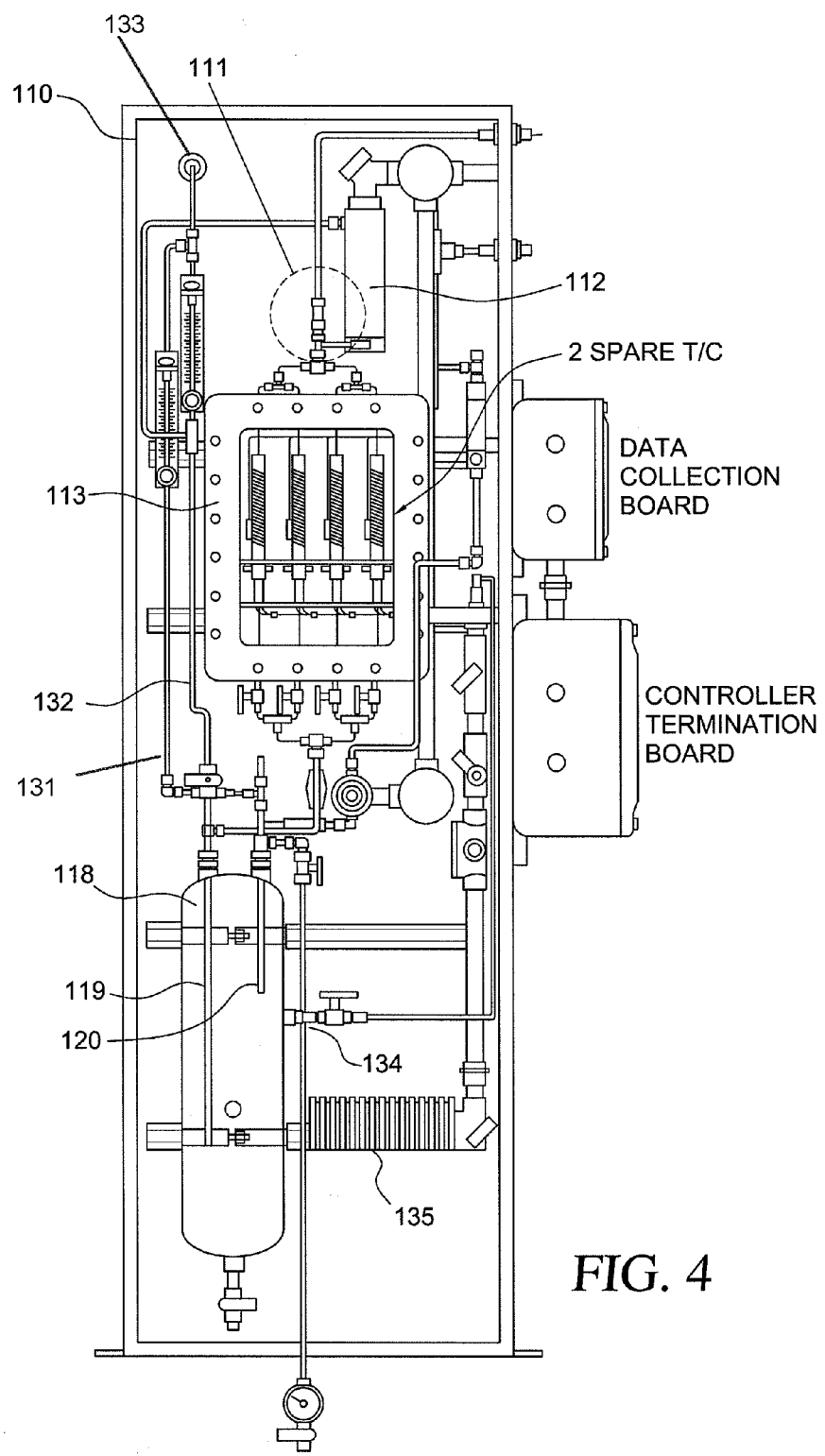
FIG. 4 is a drawing of an alternative embodiment of according to the invention.

For example, FIG. 4 illustrates and alternative embodiment of a vaporizer cabinet which differs somewhat from vaporizer 2 shown in FIG. 2. The vaporizer shown in FIG. 4 is similar in most respects to the vaporizer shown in FIG. 2. However, the embodiment of FIG. 4 uses a four-cartridge heater similar to the one illustrated in FIG. 3 and various other components are configured differently.

In particular, as shown in FIG. 4, LNG is input to the vaporizer cabinet 110 through inlet port 111 located near the top of the cabinet 110. A first stage vaporizer 112 receives a portion of the LNG and a second stage 113 receives the balance of the LNG. It should be noted that the pipe lengths for the pipes bringing LNG into the cabinet from the header pipe 3 (FIG. 1) are kept as short as possible to minimize any heating of the LNG within the inlet pipes. The second stage vaporizer 113 utilizes four cartridge heaters as shown in FIG. 3. Both the first and second stages heat the LNG and convert it to vapor gas which is accumulated in the accumulator tank 118. Also, connected to each of the first and second stages, 112 and 113, as well as the accumulator tank 118, is speed loop tubing 131 and 132 that exhausts from the cabinet 110 at outlet 133 to an LNG vapor return line (not shown). Heater 135 is located within the LNG vaporizer cabinet to keep the outlet tubes at or above a minimum temperature, for example, such that the gas within the outlet tubes remains in gaseous form.

Additionally, with respect to the embodiment shown in FIG. 4, the system pressure is monitored, as opposed to monitoring the pressure into the chromatograph, as is the case in regard to the embodiment of FIG. 1. In particular, vapor pressure is sampled at approximately the middle of accumulator tank 118. The vapor is removed through port 134 and the pressure is measured. Accordingly, by monitoring the system pressure data is provided with respect to the unloading pump sequences, pressures and pump failures, for example, as the LNG is being pumped from tanker 1 (FIG. 1). Also, in the embodiment of FIG. 4, the speed loop vapor, i.e., used to maintain a constant flow through the system, as discussed above with respect to the embodiment of FIG. 1, is taken from the discharge port of the accumulator tank 118 in order to promote a more fully mixed sample.

Modifications to the embodiments of FIGS. 2 and 4 can been made to even more closely monitor the system pressure. For instance, during tanker offloading, for example from tanker 1 (FIG. 1) into storage tanks 4, the BTU value calculations are affected by things, such as changes in tanker pump pressure and variations in storage tank filling levels. Specifically, events such as these change the speed loop flow rate which, in turn, can affect the value of the BTU calculation. Thus, by carefully monitoring and controlling the flow rate in the speed loop, these types of anomalies are detected and accommodated.

It has also been recognized that when one or more of the tanker pumps suddenly begin pumping, or otherwise change their pump rate, the BTU value reading is also affected in similar fashion to that mentioned above. Accordingly, in accordance with a further embodiment, an additional device can be added within the LNG cabinet to assist in controlling the flow rate. For example, a flow controller (not shown), such as a Brooks 5850i Mass Flow Controller from Brooks Instrument of Hatfield, Pennsylvania, can be included within the LNG cabinet to control the flow rate within the speed loop. The location of the flow control device within the speed loop is not critical. However, one viable location is, for example, on tubing 21 at the output of the accumulator 18.

It would be understood for a person having ordinary skill in the art that a device or method incorporating any of the additional or alternative details mentioned above would fall within the scope of the present invention as determined based upon the claims below and any equivalents thereof.

Other aspects, objects and advantages of the present invention can be obtained from a study of the drawings, the disclosure and the appended claims.

What is claimed is:

1. A device for sampling and vaporizing liquid natural gas, comprising:
 a vaporizer operable to receive liquid natural gas and convert the received liquid natural gas into vapor gas;
 an accumulator connected to said vaporizer and operable to receive and mix the vapor gas;
 a speed loop connected to a discharge port of the accumulator; and
 a pressure reducer operable to receive vapor gas from the accumulator and reduce the pressure of the vapor gas to a level permitting non-damaging delivery thereof to a measuring device operable to determine the constituent components of the vapor gas.

2. A device as claimed in claim 1, further comprising at least one sample tank for receiving and storing vapor gas samples from the accumulator, and a second speed loop including a vapor return line for vapor gas bypassing the at least one sample tank.

3. A device as claimed in claim 1, wherein the speed loop comprises a vapor return line.

4. A device as claimed in claim 1, wherein said accumulator comprises:

an inlet port located at a top portion of said accumulator into which the vapor gas from said first vaporizer is received;

an input tube within said accumulator and connected to said input port;

an outlet port located at the top portion of said accumulator out from which vapor gas from within said accumulator is withdrawn; and an output tube within said accumulator and connected to said outlet port.

5. A device as claimed in claim 4, wherein said input tube is longer than said outlet tube and directs inputted vapor gas against an interior wall of said accumulator.

6. A device as claimed in claim 1, wherein the vaporizer comprises a top inlet port for receiving the liquid natural gas.

7. A device as claimed in claim 1, comprising a second vaporizer.

* * * * *